US00PP20149P2

(12) United States Plant Patent
Saxena et al.

(10) Patent No.: US PP20,149 P2
(45) Date of Patent: Jul. 7, 2009

(54) NEW AND DISTINCT SOMACLONAL VARIETY OF ROSE SCENTED *GERANIUM*

(50) Latin Name: *Pelargonium graveolens*
Varietal Denomination: Parimal

(75) Inventors: Gauri Saxena, Lucknow (IN); Suchitra Banerjee, Lucknow (IN); Laiq ur Rahman, Lucknow (IN); Gopal Rao Mallavarapu, Lucknow (IN); Srikant Sharma, Lucknow (IN); Suman Preet Singh Khanuja, Lucknow (IN); Sushil Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/539,992

(22) Filed: Mar. 30, 2000

(51) Int. Cl.
*A01H 5/00* (2006.01)

(52) U.S. Cl. ..... Plt./324

(58) Field of Classification Search ..... Plt./324
See application file for complete search history.

(56) References Cited

U.S. PATENT DOCUMENTS

PP17,422 P2 * 2/2007 Westhoff ..... Plt./332

OTHER PUBLICATIONS

MPEP Chapter 1600—Plant Patents; 11 pages.*

* cited by examiner

*Primary Examiner*—Kent Bell
(74) *Attorney, Agent, or Firm*—Abelman, Frayne & Schwab

(57) ABSTRACT

A new and distinct somaclone of rose scented *geranium Pelargonium graveolens* christened 'Parimal' characterized by distinct morphology and improved oil yield determining parameters.

7 Drawing Sheets

Field

Figure 1:
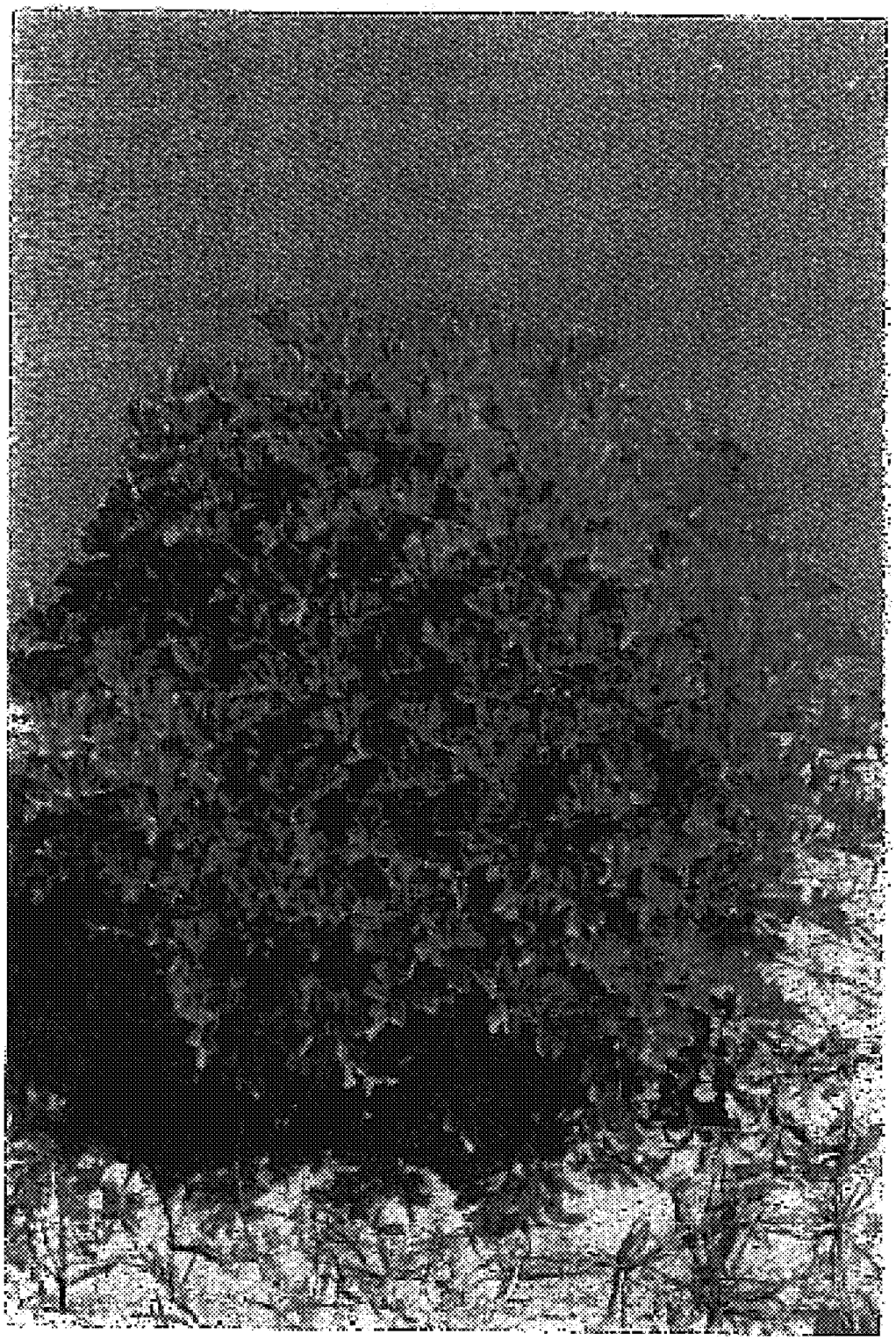

The invention provides a new distinct somaclone of rose scented *geranium P. graveolens* christened as 'Parimal' characterized by distinct morphology and improved oil yield determining parameters. The said novel somaclone has been developed from callus through in vitro tissue culture technique, without enforced mutagenesis. The plant possesses characteristic leaf morphology, vigorous growth, improved oil content per plant, herb yield and oil yield. The oil produced by this somaclone resembles the oil produced by the commercial type of bourbon *geranium* oil in that has equivalent ratio of citronellol and geraniol.

BACKGROUND OF THE INVENTION

The present invention relates to a new and distinct somaclone of rose scented *geranium Pelargonium graveolens* a member of the family Geraniaceae, which is a stable somaclone of the Indian cultivar Hemanti. The oil of *geranium* finds extensive use in perfumery, cosmetics, food and pharmaceutical industries (Narayana, 1986). *Geranium* was introduced in India in the beginning of this century and since then its cultivation and production of oil remained restricted to the high altitude regions of Ootacamund, Kodaikanal and Yercaud areas in South India (Narayana, 1986). India produces hardly 5 tonnes of *geranium* oil annually as against its own requirement of approximate 100 tonnes per year (Narayana 1986). The production of oil has declined gradually over the years and much of the requirement is met by imports. This may be due to narrow genetic base, resulting partially from sexual infertility, vegetative mode of propagation and restricted area of cultivation.

In India, two cultivars of *geranium* are mainly known; these are the types that produce Algerian or Tunisian quality and the Bourbon or the Reunion quality of *geranium* oils; these are given the names *Pelargonium×graveolens* cv Hemanti and *Pelargonium×graveolens* cv Bipuli, respectively. The cultivar Hemanti was found to be more adaptive than the cultivar Bipuli both in the hilly regions as well as in the unconventional areas of the plains. On the other hand, the cultivar Bipuli scored better than the Hemanti mainly because of its better oil yield and improved organoleptic value of the oil. The perfumery value of *geranium* oil is mainly determined by the ratio of citronellol and geraniol and almost equal contents of these two major terpenoid components is generally considered to be the characteristic of the best quality *geranium* oil.

In an attempt to extend the area of cultivation of *geranium* to the Indo-gangetic plains, the better adaptive Hemanti cultivar was introduced in the Lucknow conditions in India. Subsequently, efforts were made through different biotechnological methods to develop clones with high content and desirable composition of the oil. The calliclone 'Parimal 'evolved through this invention represents improvement over the wild type Hemanti parental cultivar both in terms of quality and quantity determining traits of the essential oil. This particular somaclone, being consistently conditions, can offer an improved cultivar for commercial exploitation.

OBJECTS OF THE INVENTION

The main objective of the inventin is to develop useful somaclonal variants of rose scented *geranium* christened as 'Parimal 'which are distinct, stable and uniform through successive generations.

Another object is to develop somaclonal variants yielding high quality and quantity of essential oil.

SUMMARY OF THE INVENTIONS

Accordingly the present invention provides a novel variety of rose scented *geranium* called 'Parimal 'said plant developed through in vitro tissue culture methods from callus cultures. The invention further provides a useful somaclonal variant *'Parimal'*of rose scented *geranium* (*Pelargonium graveolens* cv. Hemanti) yielding high quality and quantity of essential oil.

DETAILED DESCRIPTIONS

In accordance with the above and other objects, the invention provides a novel somaclone of rose scented *geranium* called 'Parimal'. The said plant has been developed though in vitro tissue cultured on modified Murashige and Skoog's medium (MS), 1962.

The invention further provides a useful somaclonal variant 'Parimal' of rose scented *geranium* (*Pelargonium graveolens* cv. Hemanti) having the following morphological characteristics.

Parentage: *Pelargonium graveolens* cultivar Hemanti.

Propagation: Exclusively vegetative propograted through terminal stem cuttings.

Time to initiate roots: 15–20 days.

Time to produce a rooted young plant through terminal stem cuttings: 30–35 days.

Terminal stem cuttings: 30–35 days.

Root description: Fibrous, brown in color.

Rooting habit: Freely branching, dense.

Plant description:

*General appearance.*—Upright, with larger and dense spreading canopy.

*Growth branching habit.*—Vigorous, showing extensive basal tillering.

*Plant length.*—85–95 cm.

Growth habit. —Spreading, round canopy.

*Plant height, to top of foliar plane.*—~46 cm.

*Stem.*—Green, internodes 8–9 cms long, nodes pinkish

*Main branches.*—Length about 85 cm. diameter about 1.1 cm internode length about 4 cm. texture pubescent, color 138D, color at nodes 75C.

*Lateral branches.*—Length about 70 cm. diameter about 0.7 cm, intermode length about 8 cm. texture pubescent, color 138D.

*Leaves.*—Number per branch 25. Arrangement Alternate. Length ~6 cm. Width ~5 cm. Texture pubescent. Shape thick, serrated with round lobes. Apex obtuse. Base cordate. Number of Primary lobes 3. Secondary lobes 12–15. Tip Blunt. Leaf area 20–28 $cm^2$. Texture (upper surface) pubescent. Texture (lower surface) pubescent. Petiole ~8 cm (pinkish). Morphological marker Less dentated leaf morphotype (Ldl). Leaf/stem ratio (L/S) 2.1. Herb yield/plant 4.5 kgs. % oil content 0.18 (mean). Oil yield/plant 7.1 gms. (mean). Oil yield (kg/ha) 71.1 (mean).

*Flower.*—No flowering entire lifetime.

*Seed.*—No seed formation.

Disease Resistance: Exhibited no specific susceptibility towards the commonly occurring fungus.

This invention further provides the useful somaclonal variant "Parimal" of rose scented *geranium* (*P. graveolens* cv. Hemanti) having the following essential oil quality determining characteristics. The average and mean percentage of the respective constituents of the essential oil are provided hereinbelow:

| Essential oil constituents | Percentage (%) |
|---|---|
| Linalool | 9.1 |
| Cis + Trans rose oxide | 0.60 |
| Menthone | 0.2 |
| Isomenthone | 7.8 |
| Citronellol | 27.6 |
| Geraniol | 22.6 |
| Citronellyl formate | 5.9 |
| Geranyl formate | 2.1 |
| Citronellyl acetate | 0.2 |
| β-caryophyllene | 0.2 |
| 6,9 guaiadiene | 0.6 |
| citronellyl butyrate | 1.0 |
| 10 Epi-γ-eudesmo | 7.3 |
| Citronellyl tiglate | 0.8 |

This invention further provides the said somaclone "Parimal" which exhibited uniqueness with respect to the following RAPD primers:MAP-05, MAP-12, MAP-15 and MAP-16.

The methods and examples for the development of the said novel plant "Parimal" are provided herein below, for illustration of the invention and should not be construed as limitations on the concept of the invention. Modifications that may be apparent to those skilled in the art are deemed to fall within the scope of the present invention.

BRIEF DESCRIPTION OF THE ACCOMPANYING DRAWINGS

The invention is further illustrated with reference to the following drawings wherein:

FIG. 1 Field grown plant of somaclone "Parimal" having large round canopy and profuse branching.

Figure 2:
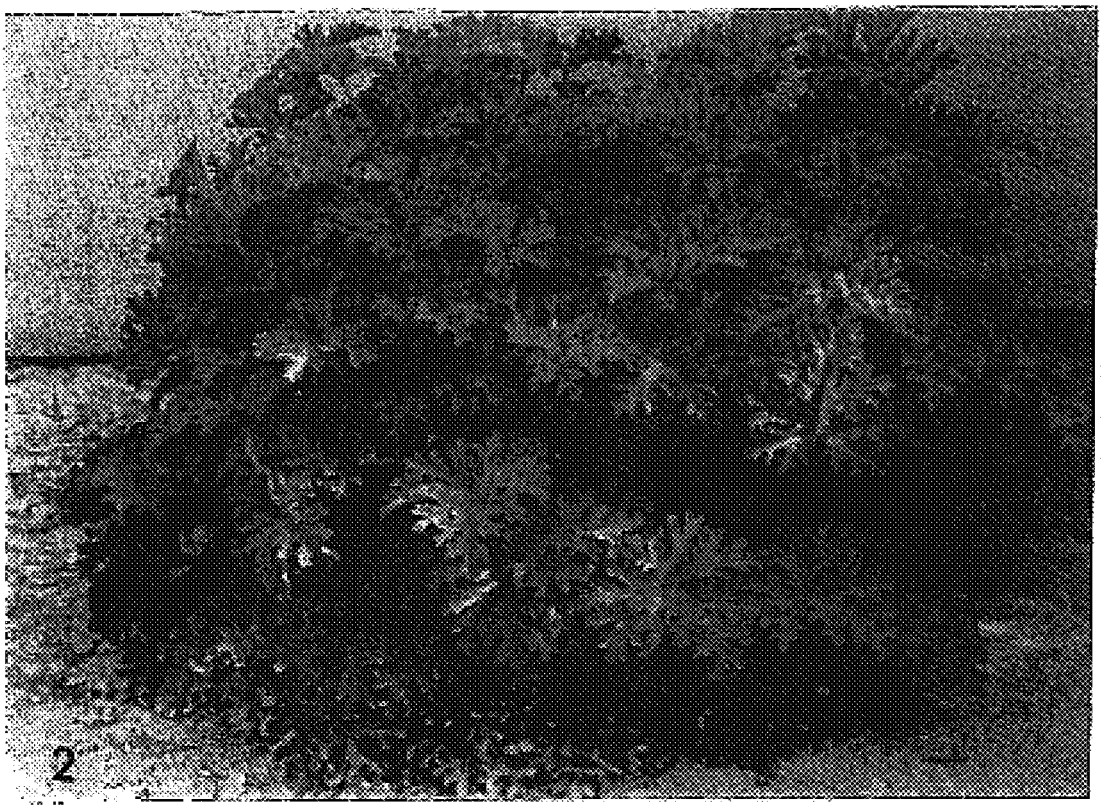

FIG. 2 Field grown plant of wild type parent spreading prostrate canopy and comparatively less branching.

Figure 3:
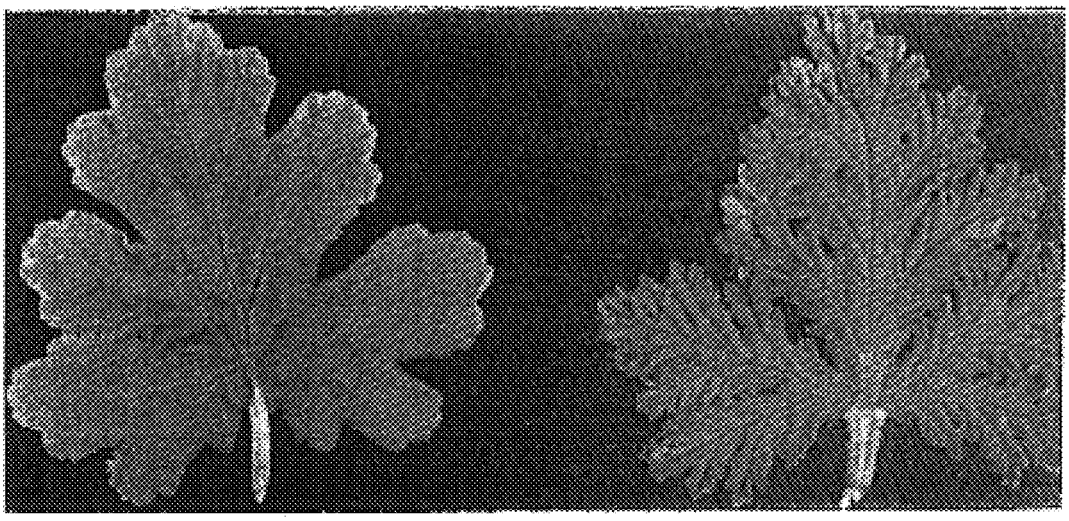
Figure 4A:
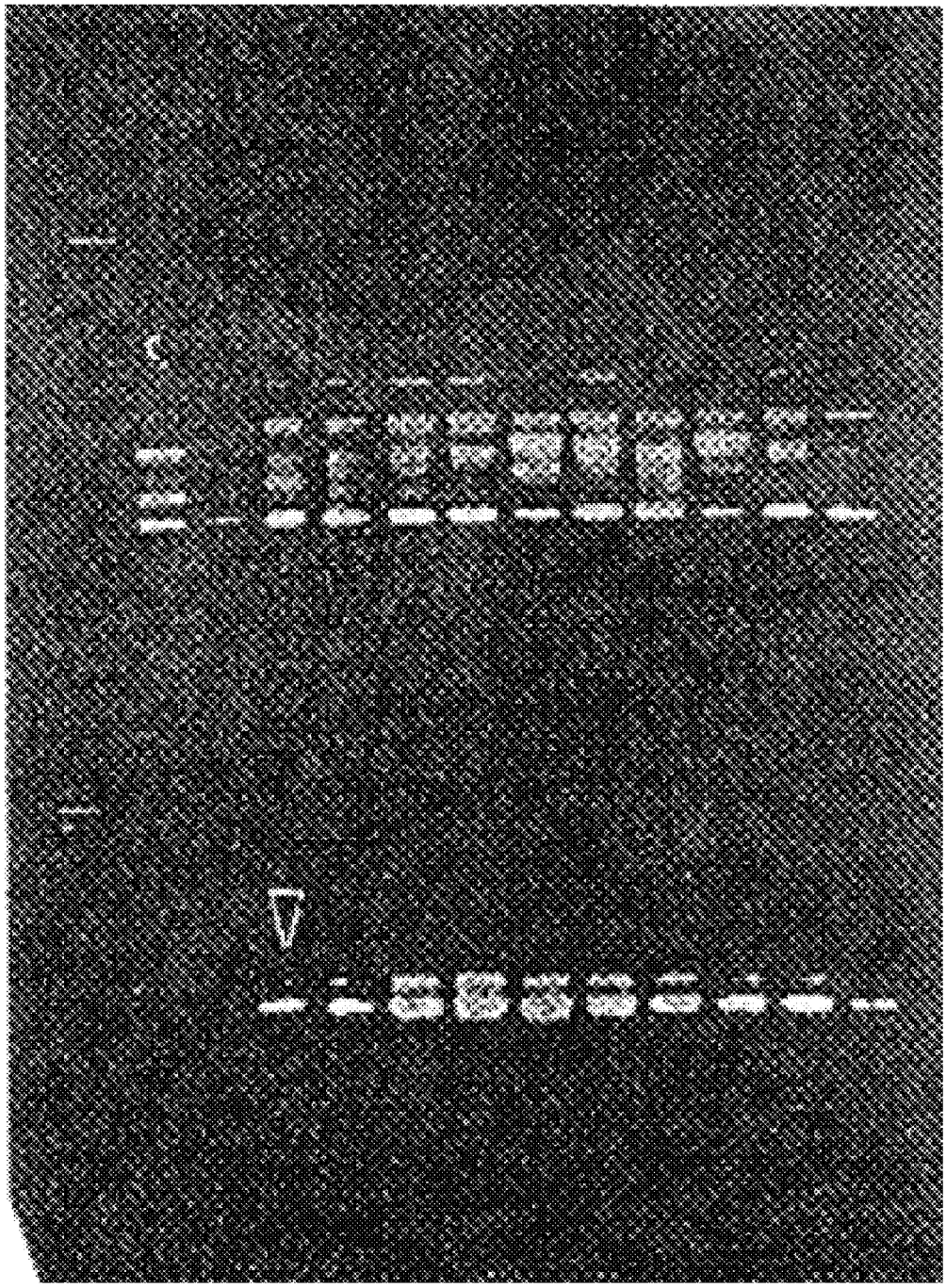
Figure 4B:
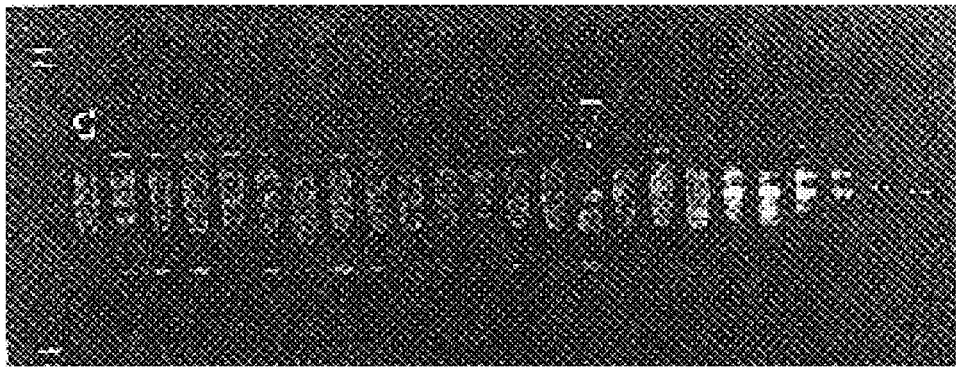
Figure 4C:
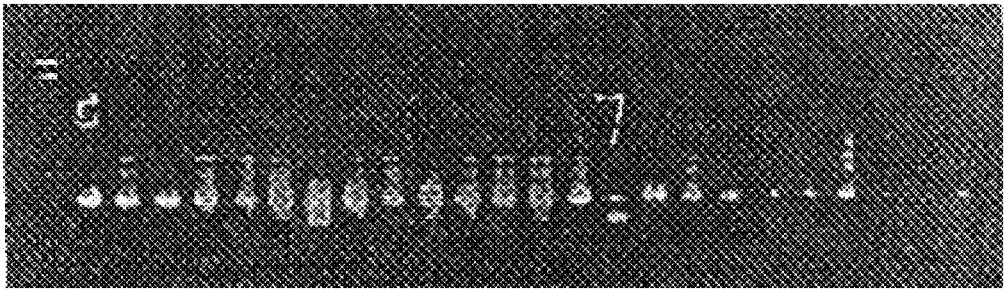
Figure 4D:
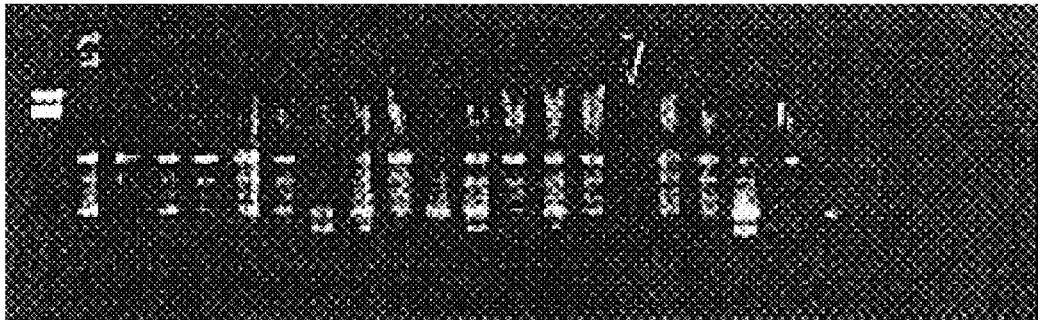

FIG. 3 Leaves of somaclone "Parimal" and wild type showing comparatively less dentation in the leaf of the former than that in the latter.

FIG. (a–d): Variation in the RAPD profiles of wild type parent (C) with that of the selected somaclone "Parimal" (marked with (→)arrow); a:primer MAP-5; b:primer MAP-12; c:primer MAP-15; d: primer MAP-16.

Methods for development of the novel somaclonal variant "Parimal":

Healthy robust shoots, raised by subculturing the organogenic calli on modified MS medium with concentrations of BAP and NAA, were transferred to half strength MS medium with a concentration of indole butyric acid (UBA) for rhizogenesis. The stem explants were cultured on modified Murashige and Skoog's medium (MS), 1962 containing the following (in mg/L)-$NH_4NO_3$ (1650), $KNO_3$ (1900), $CaCl_2.2H_2O$ (400), $MgSO_4.7H_2O$ (370), $KH_2PO_4$ (170), $Na_2EDTA.2H_2O$ (7.2), $FeSO_4.7H_2O$ (27.8), $MnSO_4.4H_2O$ (22.3), $ZnSO_4.7H_2O$ (8.6), $H_3BO_3$ (6.2), KI (0.83), $Na_2MoO_4.2H_2O$ (0.25), $CuSO_4.5H_2O$ (0.025), $CoCl_2.6H_2O$ (0.025), Glycine (2.0), Nicotinic acid (0.5), Pyrodoxine HCl (0.5) and Thiamine HCl (0.1) with proportion of naphthelene acetic acid (NAA) and Kinetin (Kn)[2:1]. The best organogenesis (85%) could be achieved by substituting Kinetin with 6-Benzylaminopurine (BAP).

The rooted plants were initially hardened under glass house conditions and were subsequently transferred to the field in the month of October 1996, in replicated trials. Based on the superior performance for vigorous growth resulting from extensive branching and enlarged canopy size, comparatively better oil yield over that of the control wild type cultivar and distinctively improved oil quality in terms of the major terpenoid constituents, the plant of this invention (Somaclone "Parimal") was selected for further observation and evaluations. During the monsoon seasons of 1996-97, this selected somaclone along with control parent were maintained under glass-house conditions through stem-cuttings which also maintained clonal purity. The selected clone "Parimal" was grown in field in replicated trials along with its parent Hemanti cultivar for two consecutive winter-summer seasons of 1997-98 and 1998-99, while during the intermediate monsoon season, they were maintained under glass-house conditions. The clone "Parimal" maintained its vigorous growth through extensive branching, better oil content and improved oil quality over the three consecutive years. The characteristics of this particular clone (in terms essential oil quantity and quality determining traits) in relation to that of the control parent and other clones have been represented in Tables-2 and 3. The results clearly demonstrate the outstanding performance of clone "Parimal" over that of the control wild type parent and other selected clones under Lucknow field conditions, indicating the feasibility of its commercial cultivation in the indo-gangetic plains. It is pertinent to mention ere that the oil profile of somaclone "Parimal" is superior than that of the wild type parent in having equal content of citronellol and geraniol which is a critical characteristic of best quality commercial *geranium* oil. The field grown plant of "Parimal" having large round canopy is shown in FIG. 1 and FIG. 2 depicts the wild type parent. The leaves of "Parimal" are as shown in FIG. 3.

Evidences of uniformity and stability

The somaclone "Parimal" has remained stable and uniform for its morphological characters and showed consistency in performance for various oil yield and quality determining attributes during its field evaluation under Lucknow conditions over three consecutive years of 1996-97, 1997-98 and 1998-99 are depicted in (Tables 1–3).

Morphological description of the somaclone "Parimal" and its wild type parent

1) Genus — *Pelargonium*
2) Species — *graveolens*
3) Family — Geraniaceae
4) Common name — rose-scented *geranium*

TABLE 1

Comparative analysis of oil yield and quality determining traits in the field grown morphologically distinct somaclones, "Parimal" and wild type *Pelargonium graveolens* CV. Hemanti (control).

| Soma-clone desig-nation | Morpho-types | Oil yield/ plant (g) | % contents of major terpenoids in the essential oil of geranium | |
|---|---|---|---|---|
| | | | Linalool | Cis + trans rose oxide |
| A | Highly | 4.5 ± 0.5 | 1.1 ± 0.2 | 1.6 ± 0.4 |
| B | dentated | 3.3 ± 0.7 | 1.1 ± 0.2 | 1.3 ± 0.3 |
| C | leaf | 8.6 ± 3.7 | 0.9 ± 0.1 | 1.2 ± 0.2 |
| D | | 4.6 ± 1.2 | 1.0 ± 0.3 | 0.9 ± 0.3 |
| Parimal | Less dentated leaf | 11.3 ± 2.8 | 9.1 ± 1.6 | 0.6 ± 0.12 |
| L | Less | 8.0 ± 4.0 | 8.5 ± 2.8 | 0.6 ± 0.1 |
| M | dentated | 4.5 ± 0.8 | 7.8 ± 1.5 | 0.7 ± 0.2 |
| N | leaf | 5.1 ± 1.6 | 7.5 ± 1.3 | 0.6 ± 0.2 |
| W (control) | Highly dentated | 3.8 ± 0.33 | 0.7 ± 0.1 | 1.5 ± 0.3 |

TABLE 1-continued

Comparative analysis of oil yield and quality determining traits in the field grown morphologically distinct somaclones, "Parimal" and wild type *Pelargonium graveolens* CV. Hemanti (control).

| Soma-clone desig-nation | Morpho-types | % contents of major terpenoids in the essential oil of geranium | | |
|---|---|---|---|---|
| | | Isomenthone | Citronellol | Geraniol |
| A | Highly | 9.6 ± 1.8 | 49.8 ± 1.4 | 2.0 ± 0.5 |
| B | dentated | 9.0 ± 2.5 | 52.6 ± 1.9 | 2.3 ± 0.6 |
| C | leaf | 10.3 ± 1.3 | 51.7 ± 1.1 | 1.8 ± 0.4 |
| D | | 10.6 ± 2.1 | 48.6 ± 4.5 | 2.3 ± 1.1 |
| Parimal | Less dentated leaf | 7.8 ± 0.53 | 27.6 ± 2.1 | 22.6 ± 3.2 |
| L | Less | 7.7 ± 0.5 | 28.7 ± 4.3 | 22.3 ± 2.8 |
| M | dentated | 6.9 ± 1.5 | 29.2 ± 3.9 | 20.4 ± 2.1 |
| N | leaf | 7.1 ± 1.2 | 29.1 ± 4.4 | 19.5 ± 3.1 |
| W (control) | Highly dentated | 9.5 ± 0.1 | 53.1 ± 0.7 | 1.6 ± 0.14 |

| Soma-clone desig-nation | Morpho-types | % contents of major terpenoids in the essential oil of geranium | | | |
|---|---|---|---|---|---|
| | | Citronel-llyl formate | Geranyl formate | 6,9-guaiadiene | 10-epi-□-eudesmol |
| A | Highly | 13.0 ± 0.4 | 0.5 ± 0.3 | 1.3 ± 0.6 | 2.9 ± 0.5 |
| B | dentated | 11.7 ± 1.3 | 0.3 ± 0.15 | 1.3 ± 0.4 | 3.0 ± 0.7 |
| C | leaf | 11.1 ± 0.9 | 0.23 ± 0.03 | 1.3 ± 0.4 | 2.9 ± 0.5 |
| D | | 10.2 ± 2.7 | 0.6 ± 0.45 | 1.2 ± 0.4 | 4.4 ± 1.4 |
| Parimal | Less dentated leaf | 5.9 ± 0.2 | 2.1 ± 0.4 | 0.6 ± 0.12 | 7.3 ± 0.95 |
| L | Less | 5.6 ± 0.7 | 2.0 ± 0.2 | 0.7 ± 0.1 | 7.4 ± 1.1 |
| M | dentated | 4.8 ± 0.7 | 1.8 ± 0.2 | 0.7 ± 0.03 | 8.6 ± 1.8 |
| N | leaf | 4.7 ± 0.8 | 1.8 ± 0.6 | 0.6 ± 0.05 | 8.2 ± 1.6 |
| W (control) | Highly dentated | 12.1 ± 0.6 | 0.23 ± 0.03 | 2.0 ± 0.2 | 3.2 ± 0.2 |

TABLE 2

Morphological characteristics of somaclone "Parimal" and its wild type parent

| Morphological parameters | Parimal | Wild type |
|---|---|---|
| Plant height | 85-95 cm | 35-45 cm |
| Growth habit | spreading, round canopy | Spreading prostrate |
| Stem | green, internodes 8-9 cms long, nodes pinkish | Greenish magenta purplish at the nodes, 5-10 mm in diameter, densely hairy |
| Branches | 91-101 | 10-45 |
| Leaf | | |
| Number per branch | 10-25 | 25-30 |
| Texture | pubescent | pubescent |
| Shape | thick, serrated with round lobes | thick hairy highly serrated |
| Number of | | |
| primary lobes | | 3 to 5 |
| secondary lobes | 3 | 15-30 |
| | 12-15 | |
| Tip | Blunt | Blunt |
| Leaf area | 20-28 $cm^2$ | 30-36 $cm^2$ |
| Petiole | ~8 cm (pinkish) | ~5 cm (green) |

TABLE 3

Oil yield and quality determining traits of somaclone "Parimal" and its wild type parent.

| | Trait | Somaclone "Parimal" | Wild type |
|---|---|---|---|
| 1. | Morphological marker | Less dentated leaf morphotype (Ldl) | Highly dentated leaf morphotype (Hdl) |
| 2. | Leaf/stem ratio (L/S) | 2.1 | 1.5 |
| 3. | Herb yield/plant | 4.5 kgs. | 1.9 kgs |
| 4. | % oil content | 0.18 | 0.15 |
| 5. | Oil yield/plant | 7.1 gms. | 2.5 gms. |
| 6. | Oil yield (kg/ha) | 71.1 | 25.1 |
| 7. | Oil quality | | |
| i) | Linalool | 9.1 | 0.7 |
| ii) | Cis + Trans rose oxide | 0.60 | 1.5 |
| iii) | Menthone | 0.2 | 0.3 |
| iv) | Isomenthone | 7.8 | 9.5 |
| v) | Citronellol | 27.6 | 53.1 |
| vi) | Geraniol | 22.6 | 1.6 |
| vii) | Citronellyl formate | 5.9 | 12.1 |
| viii) | Geranyl formate | 2.1 | 0.2 |
| ix) | Citronellyl acetate | 0.2 | 0.9 |
| x) | β-caryophyllene | 0.2 | 1.5 |
| xi) | 6,9 guaiadiene | 0.6 | 2.0 |
| xii) | citronellyl butyrate | 1.0 | 2.2 |
| xiii) | 10 Epi-γ-eudesmol | 7.3 | 3.2 |
| xiv) | Citronellyl tiglate | 0.8 | 1.6 |

Type and frequency of variants during multiplication and maintenance of the somaclone No variants has been recovered during multiplication, maintenance and testing of the somaclone "Parimal" in experimental plots, screened carefully in 1996-97, 1997-98 and 1998-99 winter-summer cropping seasons. The three year's observations on somaclone "Parimal" were statistically analysed for significance of differences in the morphological oil yield determining attributes and the concentrations of 9 *geranium* oil quality determining terpenoid constituents. The intraclonal variation in clone "Parimal" was found statistically insignificant over three year's field trial.

Statement of distinction

The somaclones "Parimal" are distinct in having large round canopy, less dentated round leaf morphology, extensive branching and absence of flowering (Table 1). Its oil profile is distinct from the wild type parent cultivar in having higher proportion of geraniol and lower proportion of citronellol, lower content of cis+trans rose oxide and citronellyl formate, 6,9-guadiene, higher content of linalool, geranyl formate and 10-epi-y endesmol (Table-2). Its RAPD profile was different from the wild type parent in certain aspects while had certain features common in both.

Characterization through RAPD markers

Using 13 random primers (MAP 01 to MAP 16) with following sequence description a comparison was made for somaclone "Parimal" and its wild type parent to establish the relatedness between them.

| Primer | Base Sequence |
|---|---|
| MAP01 | GTGCAATCAG SEQ. ID NO: 1 |
| MAP02 | AGGATACGTG SEQ. ID NO: 2 |
| MAP04 | AAGATAGCGG SEQ. ID NO: 3 |
| MAP05 | GGATCTGAAC SEQ. ID NO: 4 |
| MAP06 | TTGTCTCAGG SEQ. ID NO: 5 |

-continued

| Primer | Base Sequence |
|---|---|
| MAP07 | GTCCTACTCG SEQ. ID NO: 6 |
| MAP09 | TGCGCGATCG SEQ. ID NO: 7 |
| MAP10 | AACGTACGCG SEQ. ID NO: 8 |
| MAP11 | GCACGCCGGA SEQ. ID NO: 9 |
| MAP12 | CACCCTGCGC SEQ. ID NO: 10 |
| MAP14 | GGACTCCACG SEQ. ID NO: 11 |
| MAP15 | AAGATAGCGG SEQ. ID NO: 12 |
| MAP16 | CTATCGCCGC SEQ. ID NO: 13 |

This analysis could narrow down with usage of six MAP primers (MAP 04, MAP 05, MAP 10, MAP 14, MAP 15, MAP 16) which in turn were utilized for genotypic pair analysis in order to assess genetic/molecular distances. The following table 4 gives the similarity index between the two genotypes in paired test.

TABLE 4

Similarity percentage for amplified bands (paired analysis) of somaclone "Parimal" and wild type parent

| Primer | Genotypic pair (somaclone "Parimal"/wild type) |
|---|---|
| MAP 04 | 93 |
| MAP 05 | 80 |
| MAP 10 | 60 |
| MAP 14 | 90 |
| MAP 15 | 83 |
| MAP 16 | 66 |

It is evident from similarity indices (paired test) that somaclone "Parimal" and wild type parent are genetically distinguishable (Table 4). Further, the primer MAP 10, MAP 14 showed least similarity while primers MAP 04 and MAP15 showed close relatedness. The primers MAP05 and MAP16 showed intermediate degree of similarity. These observations on percent similarity confirm the relatedness of somaclone "Parimal" with the wild type parent, at the same time highlight the distinctness of the former at the genetic level. The complete RAPD profile for PCR amplified DNA segments using 12 primers is available providing evidence of distinctiveness of the clone with respect to the control parent as shown in FIG. 4.

Advantages:

1. "Parimal" is well adaptive to the unconventional area of cultivation i.e. northern Indian plains.
2. "Parimal" represents improvement over its wild type parental cv. "Hemanti" with resepect to the following quantitative traits: (a) Larger and denser canopy; (b) Greater herb yield; (c) Higher leaf:stem ratio; (d) Higher oil content; and (e) Much higher oil yield (both on per plant and per hectare basis).
3. "Parimal" represent improvement over its wild type parental cv. "Hemanti" with respect to following major essential oil quality determining traits: (a) About equal citronellol:geraniol ratio; (b) Higher rhodinol content; (c) Higher linalool concentration; (d) Lower concentration of 6,9-guaiadiene.
4. The somaclone "Parimal" showed consistency in performance for all the above mentioned oil yield and quality determining attributes during its field evaluation under Lucknow conditions over three consecutive years.
5. "Parimal" showed distinctiveness even at genetic level with respect to RAPD primers, MAP-05, MAP-12, MAP-15 and MAP-16.

SEQUENCE LISTING

<160> NUMBER OF SEQ ID NOS: 13

<210> SEQ ID NO 1
<211> LENGTH: 10
<212> TYPE: DNA
<213> ORGANISM: artificial sequence
<220> FEATURE:
<223> OTHER INFORMATION: random primers

<400> SEQUENCE: 1 gtgcaatcag 10

<210> SEQ ID NO 2
<211> LENGTH: 10
<212> TYPE: DNA
<213> ORGANISM: ARTIFICIAL SEQUENCE
<220> FEATURE:
<223> OTHER INFORMATION: random primer

<400> SEQUENCE: 2 aggatacgtg 10

<210> SEQ ID NO 3
<211> LENGTH: 10
<212> TYPE: DNA
<213> ORGANISM: artificial sequence
<220> FEATURE:
<223> OTHER INFORMATION: random primer

<400> SEQUENCE: 3 aagatagcgg 10

<210> SEQ ID NO 4
<211> LENGTH: 10
<212> TYPE: DNA
<213> ORGANISM: artificial sequence
<220> FEATURE:
<223> OTHER INFORMATION: random primer

<400> SEQUENCE: 4 ggatctgaac 10

<210> SEQ ID NO 5
<211> LENGTH: 10
<212> TYPE: DNA
<213> ORGANISM: artificial sequence
<220> FEATURE:
<223> OTHER INFORMATION: random primer

<400> SEQUENCE: 5 ttgtctcagg 10

<210> SEQ ID NO 6
<211> LENGTH: 10
<212> TYPE: DNA
<213> ORGANISM: artificial sequence
<220> FEATURE:
<223> OTHER INFORMATION: random primer

<400> SEQUENCE: 6 gtcctactcg 10

<210> SEQ ID NO 7

-continued

<211> LENGTH: 10
<212> TYPE: DNA
<213> ORGANISM: artificial sequence
<220> FEATURE:
<223> OTHER INFORMATION: random primer

<400> SEQUENCE: 7 tgcgcgatcg 10

<210> SEQ ID NO 8
<211> LENGTH: 10
<212> TYPE: DNA
<213> ORGANISM: artificial sequence
<220> FEATURE:
<223> OTHER INFORMATION: random primer

<400> SEQUENCE: 8 aacgtacgcg 10

<210> SEQ ID NO 9
<211> LENGTH: 10
<212> TYPE: DNA
<213> ORGANISM: artificial sequence
<220> FEATURE:
<223> OTHER INFORMATION: random primer

<400> SEQUENCE: 9 gcacgccgga 10

<210> SEQ ID NO 10
<211> LENGTH: 10
<212> TYPE: DNA
<213> ORGANISM: artificial sequence
<220> FEATURE:
<223> OTHER INFORMATION: random primer

<400> SEQUENCE: 10 caccctgcgc 10

<210> SEQ ID NO 11
<211> LENGTH: 10
<212> TYPE: DNA
<213> ORGANISM: artificial sequence
<220> FEATURE:
<223> OTHER INFORMATION: random primer

<400> SEQUENCE: 11 ggactccacg 10

<210> SEQ ID NO 12
<211> LENGTH: 10
<212> TYPE: DNA
<213> ORGANISM: artificial sequence
<220> FEATURE:
<223> OTHER INFORMATION: random primer

<400> SEQUENCE: 12 aagatagcgg 10

<210> SEQ ID NO 13
<211> LENGTH: 10
<212> TYPE: DNA

-continued

```
<213> ORGANISM: artificial sequence
<220> FEATURE:
<223> OTHER INFORMATION: random primer

<400> SEQUENCE: 13

ctatcgccgc                                                          10
```

It is claimed:

1. A rose scented *Geranium* plant named 'Parimal', as herein illustrated and described.

* * * * *